(12) United States Patent
Colurciello et al.

(10) Patent No.: US 9,655,367 B2
(45) Date of Patent: May 23, 2017

(54) DISINFECTING COMPOSITION AND WIPES WITH REDUCED CONTACT TIME

(71) Applicant: Lonza, Inc., Allendale, NJ (US)

(72) Inventors: Andrew Colurciello, Newburgh, NY (US); David Koehl, Bethlehem, PA (US)

(73) Assignee: LONZA, INC., Allendale, NJ (US)

( * ) Notice: Subject to any disclaimer, the term of this patent is extended or adjusted under 35 U.S.C. 154(b) by 171 days.

(21) Appl. No.: 14/532,842

(22) Filed: Nov. 4, 2014

(65) Prior Publication Data
US 2015/0125502 A1 May 7, 2015

Related U.S. Application Data

(60) Provisional application No. 61/900,797, filed on Nov. 6, 2013.

(51) Int. Cl.
| | |
|---|---|
| *A01N 47/44* | (2006.01) |
| *A01N 33/12* | (2006.01) |
| *A01N 25/34* | (2006.01) |
| *A61L 2/18* | (2006.01) |
| *C11D 1/62* | (2006.01) |
| *C11D 3/48* | (2006.01) |
| *C11D 17/04* | (2006.01) |
| *C11D 3/30* | (2006.01) |

(52) U.S. Cl.
CPC .............. *A01N 47/44* (2013.01); *A01N 33/12* (2013.01); *A61L 2/18* (2013.01); *C11D 1/62* (2013.01); *C11D 3/30* (2013.01); *C11D 3/48* (2013.01); *C11D 17/049* (2013.01)

(58) Field of Classification Search
USPC ............................................... 424/78.08, 404
See application file for complete search history.

(56) References Cited

U.S. PATENT DOCUMENTS

| | | |
|---|---|---|
| 5,185,145 A | 2/1993 | Eggensperger et al. |
| 2004/0185028 A1 | 9/2004 | Hu et al. |
| 2006/0166849 A1 | 7/2006 | Kilkenny et al. |
| 2010/0086514 A1 | 4/2010 | Liu et al. |
| 2012/0087963 A1 | 4/2012 | Evans et al. |

FOREIGN PATENT DOCUMENTS

| | | |
|---|---|---|
| EP | 1256276 A1 | 11/2002 |
| EP | 2548585 A1 | 1/2013 |
| WO | 2013/005036 A1 | 1/2013 |

*Primary Examiner* — Walter Webb
(74) *Attorney, Agent, or Firm* — Lucas & Mercanti LLP

(57) ABSTRACT

A composition having a short disinfecting contact time is disclosed. The composition contains a biguanide or guanide, a quaternary ammonium compound and a basic compound in a specific weight ratio to one another. Compositions having less than a two minute disinfection time are disclosed.

26 Claims, No Drawings

DISINFECTING COMPOSITION AND WIPES WITH REDUCED CONTACT TIME

CROSS-REFERENCE TO RELATED APPLICATION

This application claims priority under 35 U.S.C. §119(e) from Provisional Application No. 61/900,797, filed Nov. 6, 2013, the disclosure of which is incorporated herein by reference.

FIELD OF THE INVENTION

The present invention relates to a disinfecting composition and wipes impregnated with the composition.

BACKGROUND OF THE INVENTION

Antimicrobial compositions for decontamination, disinfection and/or sanitization must have an effective microbial kill rate to be suitable for use as decontamination, disinfection and/or sanitization compositions. These antimicrobial compositions are generally desirable to be low in corrosion to the surfaces being treated and low in odor. In addition, these compositions generally will only contain enough of the microbial control agent to be effective for a given application. Having too much of the microbial control agent does not provide any advantages to the resulting composition, essentially wasting any excess microbial control agent in the composition. Having too little microbial control agent will make the composition less effective than needed for its intended use.

One particular class of antimicrobial compositions includes quaternary ammonium compounds, also known as "quats", as a microbial control agent. Generally, quaternary ammonium compounds containing compositions have been used where disinfecting contact times of about 4 minutes or more are achievable. Contact time is the amount of time necessary to achieve an effective microbial kill rate to achieve disinfection. These quat containing disinfecting compositions may have up to about 3000 ppm of quats in the composition. Increasing the amount of quats above this level does not have much of appreciable effect in reducing the contact time below the 4 minute level.

Disinfecting compositions having shorter disinfecting times and wipes saturated with these disinfecting compositions are desirable in institutions, such as schools, and medical facilities such as hospitals. There is a need in the art for a disinfecting composition which is quat based that will have relatively short disinfecting times, preferably under 4 minutes and more preferably under 90 seconds and having at least a 5 $Log_{10}$ reduction (destroying 99.999% of specified pathogenic organisms) for *Staphylococcus aureus* and *Pseudomonas aeruginosa*. Such a composition may be characterized as a hospital grade disinfecting solution. It has been discovered that the disinfecting composition described herein, and the wipes saturated with the disinfecting composition provide an answer to that need.

SUMMARY OF THE INVENTION

In one aspect, there is provided is a disinfectant composition containing (i) an antimicrobial biguanide, monoguanide or a combination thereof; (ii) a quaternary ammonium compound or a mixture of quaternary ammonium compounds; and (iii) a basic compound. In the disinfectant composition, the weight ratio of the biguanide or monoguanide (component (i)) to the quaternary ammonium compound or a mixture of quaternary ammonium compounds (component (ii)) is in the range of about 1:1.5 to about 1:10; and the weight ratio of the biguanide or monoguanide (component (i)) to the basic compound (component (iii)) is in the range of about 1:3 to about 1:15.

In another aspect, there is provided a disinfectant composition containing (i) an antimicrobial biguanide, monoguanide or a combination thereof; (ii) a quaternary ammonium compound or a mixture of quaternary ammonium compounds; and (iii) a basic compound in which component (i) is present in the composition in an amount from about 400 ppm to about 1200 ppm; component (ii) is present in the composition in an amount from about 2000 to about 3600 ppm; and component (iii) is present in the composition in an amount from about 3000 ppm to about 7000 ppm. In these concentrations, the disinfectant composition is in a ready-to-use disinfecting composition.

In a further aspect of the present invention, provided is a wipe having a substrate which is impregnated with the disinfectant composition of the other aspects.

In an additional aspect of the present invention, provided is method of disinfecting a surface by applying the disinfectant composition to the surface for a period of time which is preferably sufficient to allow the composition to remain in contact with the surface and disinfect the surface.

These and other aspects will become apparent when reading the detailed description of the invention.

DETAILED DESCRIPTION OF THE INVENTION

It has now been surprisingly found that combining a biguanide or guanide component and a basic component with a composition containing a quaternary ammonium compound as a disinfecting agent allows a reduction in contact time to achieve disinfection.

Component (i) of the disinfectant composition is selected from among biguanides, monoguanides, and combinations thereof. Suitable biguanides are disclosed in U.S. Application Publication No. 2005/0014670. The patent publication is incorporated herein by reference in its entirety. Generally, the biguanide comprises at least two biguanide units of Formula (1):

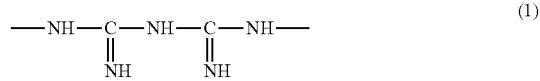

linked by a bridging group which contains at least one methylene group. The bridging group generally includes a polymethylene chain, optionally incorporating or substituted by one or more hetero atoms such as oxygen, sulfur or nitrogen. The bridging group may include one or more cyclic moieties which may be saturated or unsaturated. Typically, the bridging group is such that there are at least three, and especially at least four, carbon atoms directly interposed between two adjacent biguanide units of Formula (1). In most cases, there are not greater than ten and especially not greater than eight carbon atoms interposed between two adjacent biguanide units of Formula (1).

The polymeric biguanide may be terminated by any suitable group, such as a hydrocarbyl, substituted hydrocarbyl or an amine group or a cyanoguanidine group of the Formula (2):

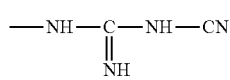
(2)

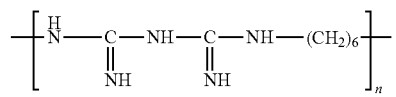
(4)

wherein n is from 4 to 20 and especially from 4 to 18. On particular example is the average value of n is about 12. Typically, the average molecular weight of the polymer in the free base form is from 1100 to 4000.

Generally, the polymeric biguanide is in the form of a salt. Typical salts are those with organic or inorganic acids, especially water-soluble salts, for example, the chloride, gluconate, acetate, stearate, carbonate, sulfate or phosphate salt, to mention a few.

The linear polymeric biguanides may be prepared by the methods disclosed in U.S. Patent Application Publication 2005/0014670. One particular commercially available is Vantocil™P, available from Arch Chemicals, Inc., a Lonza Company.

The monoguanides or guanides useable in the present invention include compound have at least one group of formula (5)

(5)

wherein each R is independently a hydrogen atom, an optionally substituted alkyl group or an optionally substituted alkoxy group.

One particular monoguanide is polymonoguanide (PMG) which typically comprises a plurality of groups of Formula (6) or salts thereof:

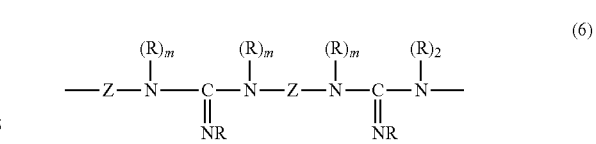
(6)

wherein: each m independently is 0 or 1; each Z independently is a $C_{2-18}$-hydrocarbyl group or a group that forms a cyclic group to the N atoms to which it is attached having the general formula (7)

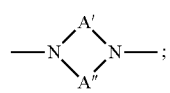
(7)

A' and A" are hydrocarbyl groups which together comprise a total of 3 to 18 carbon atoms; each R is defined as above. Each m is generally 0, when A' and A" are present.

The hydrocarbyl groups in the PMG and represented by Z, A' and A" are optionally interrupted by one or more hetero atoms or groups and optionally carry one or more substituents other than hydrogen. Interrupting atoms and groups are —O—, —S—, —NH—, —C(=O)— and phenylene. Optional substituents are hydroxy; $C_{1-4}$-alkoxy; halo, espe- When the terminating group is hydrocarbyl, it is typically an alkyl, a cycloalkyl, an aryl or an aralkyl. When the hydrocarbyl group is an alkyl group, it may be linear or branched, but is generally linear. Useable alkyl groups include $C_{1-8}$-alkyl. Examples of preferred alkyl groups include for example methyl, ethyl, n-propyl, isopropyl, n-pentyl, n-butyl, isobutyl, tert-butyl and n-octyl.

When the hydrocarbyl group is cycloalkyl, it is typically a cyclopropyl, a cyclopentyl or a cyclohexyl. When the hydrocarbyl group is aralkyl, it generally contains from 1 to 6, more typically 1 or 2 carbon atoms in the alkylene group attaching the aryl group to the biguanide. Aralkyl groups include benzyl and 2-phenylethyl groups. Aryl groups include phenyl groups.

When the terminating group is substituted hydrocarbyl, the substituent may be any substituent that does not exhibit undesirable adverse effects on the microbiological properties of the polymeric biguanide. Examples of such substituents are aryloxy, alkoxy, acyl, acyloxy, halogen and nitrile, and these groups may be present on the alkyl group, the cycloalkyl, or aralkyl group.

When the polymeric biguanide contains two biguanide groups of Formula (1), the biguanide is a bisbiguanide. The two biguanide groups are preferably linked through a polymethylene group, typically a hexamethylene group.

The polymeric biguanide preferably contains more than two biguanide units of Formula (1) and is a linear polymeric biguanide which has a recurring polymeric chain represented by Formula (3) or a salt thereof:

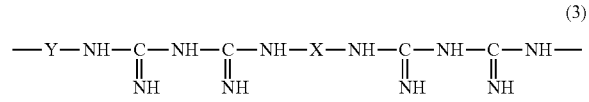
(3)

wherein X and Y represent bridging groups which may be the same or different and in which together the total of the number of carbon atoms directly interposed between the pairs of nitrogen atoms linked by Y plus the number of carbon atoms directly interposed between the pairs of nitrogen atoms linked by X is more than 9 and less than 17.

The bridging groups X and Y may be polymethylene chains, optionally interrupted by hetero atoms, for example, oxygen, sulfur or nitrogen. X and Y may also incorporate moieties which may be saturated or unsaturated. In addition, may be a cyclic group, in which case the number of carbon atoms directly interposed between the pairs of nitrogen atoms linked by X and Y is taken as including that segment of the cyclic group, or groups, which is the shortest.

The linear polymeric biguanides having a recurring polymer unit of Formula (3) are typically obtained as mixtures of polymers in which the polymer chains are of different lengths. Typically, the number of individual biguanide units is in the range of from 3 to about 80.

One particular linear polymeric biguanide is a mixture of polymer chains in which X and Y are identical and the individual polymer chains, excluding the terminating groups, are of the Formula (4) or a salt thereof:

cially chloro or bromo; nitro; amino; substituted amino; and acid groups, especially carboxy, sulpho and phosphato.

Generally, the hydrocarbyl groups in the PMG and represented by Z are $C_{2-18}$-alkylene (more preferably $C_{4-16}$-alkylene, especially $C_{6-12}$-alkylene, more especially $C_6$-alkylene); $C_{3-12}$-arylene, more preferably $C_{6-10}$-arylene, especially phenylene or naphthylene; $C_{7-12}$-arakylene (more preferably $C_{7-11}$-arylene, especially benzylene or xylyene); or a combination thereof, optionally interrupted by one or more —O—, —S—, —NH— or —C(=O)— groups.

Typically the hydrocarbyl groups represented by A' and A" are each independently $C_{2-6}$-alkylene, optionally interrupted by one or more —O—, —S—, —NH— or —C(=O)— groups, with the proviso that A' and A" comprise a total of 3 to 12 carbon atoms, preferably 3 to 6 carbon atoms, more preferably 3 or 4 carbon atoms. In one embodiment one of A' or A" is —CH$_2$— or —(CH$_2$)$_2$— and the other is —(CH$_2$)$_2$—, more especially both A' and A" are —(CH$_2$)$_2$—.

Examples of hydrocarbyl groups represented by Z include —CH$_2$C$_6$H$_4$—CH$_2$—, —CH$_2$OC$_6$H$_4$OCH$_2$—, —CH$_2$OC$_6$H$_{10}$OCH$_2$—, —(CH$_2$)$_3$—O—(CH$_2$)$_3$— and —(CH$_2$)$_2$S(CH$_2$)$_2$—.

Examples of hydrocarbyl groups represented by Z include —(CH$_2$)$_6$—, —(CH$_2$)$_8$—, —(CH$_2$)$_{12}$—, —CH$_2$CH(—CH$_3$)(CH$_2$)$_4$CH$_3$, 1,4-, 2,3- and 1,3-butylene, 2,5-hexylene, 2,7-heptylene and 3-methyl-1,6-hexylene.

Generally, all groups represented by Z are the same and are $C_{4-16}$-alkylene, more preferably $C_{4-12}$-alkylene, especially $C_{4-8}$-alkylene, more especially 1,6 hexylene.

Typically, all groups represented by R are the same and are typically all groups represented by R are H.

The nature of the terminating groups on the PMG is not believed to be critical. Terminating groups on the PMG may be amino and guanidino.

In view of the foregoing preferences the PMG preferably comprises one or more groups of Formula (8) or salts thereof

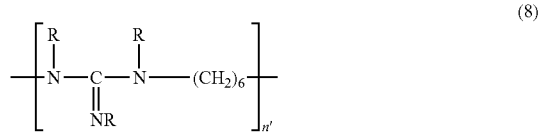

(8)

wherein: n' is 2 to 50 and typically 3 to 25.

Typically, the PMG is in the form of a salt. Salts are those with organic or inorganic acids, especially water-soluble salts, for example the chloride, gluconate, acetate or phosphate salt.

The PMGs may be prepared by known methods including by the reaction of guanidine hydrochloride with a diamine, for example of the formula H$_2$N—Z—NH$_2$, or with a mixture of such diamines, wherein Z, is as defined above.

Generally, component (a) is polyhexamethylenebiguanide or the salts thereof. Typically, component (a) is polyhexamethylenebiguanide hydrochloride salt.

Component (ii) of the disinfecting composition is a quaternary ammonium compound or a mixture of quaternary ammonium compounds. Quaternary ammonium compounds, also known as "quats", typically comprise at least one quaternary ammonium cation with an appropriate anion. Quats will generally have the general formula (9).

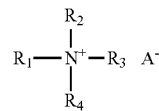

(9)

The groups $R_1$, $R_2$, $R_3$ and $R_4$ can vary within wide limits and examples of quaternary ammonium compounds that have anti-microbial properties will be well known to the person of ordinary skill in the art. $A^-$ is a monovalent anion or one equivalent of a polyvalent anion of an inorganic or organic acid. Suitable anions $A^-$ are in principle all inorganic or organic anions, in particular halides, for example chloride or bromide, carbonates, bicarbonates, carboxylates, sulfonates, phosphates or a mixture thereof.

Each group $R_1$, $R_2$, $R_3$ and $R_4$ may, for example, independently be a substituted or unsubstituted and/or straight chain or branched and/or interrupted or uninterrupted alkyl, aryl, alkylaryl, arylalkyl, cycloalkyl, (aromatic or non-aromatic) heterocyclyl or alkenyl group. Alternatively, two or more of $R_1$, $R_2$, $R_3$ and $R_4$ may together with the nitrogen atom form a substituted or unsubstituted heterocyclic ring. The total number of carbon atoms in the groups $R_1$, $R_2$, $R_3$ and $R_4$ must be at least 4. Typically the sum of the carbon atoms in the groups $R_1$, $R_2$, $R_3$ and $R_4$ is 10 or more. In a one aspect of the present invention, at least one of the groups $R_1$, $R_2$, $R_3$ and $R_4$ contains from 8 to 18 carbon atoms. For example, at least 1 and up to 4 of $R_1$, $R_2$, $R_3$ and $R_4$ can contain from 8 to 18 carbon atoms, typically 10 to 16 carbon atoms.

Suitable substituents for the groups $R_1$, $R_2$, $R_3$ and $R_4$ may be selected from the group consisting of alkyl, substituted alkyl, alkenyl, substituted alkenyl, heterocyclyl, substituted heterocyclyl, cycloalkyl, substituted cycloalkyl, aryl, substituted aryl, alkylaryl, substituted alkylaryl, arylalkyl, substituted arylalkyl. Each of the substituents on the substituted groups may be F, Br, I, —OR', —NR'R", —CF$_3$, —CN, —NO$_2$, —C$_2$R', —SR', —N$_3$, —C(=O)NR'R", —NR'C(O)R", —O(CR'R")$_r$C(=O)R', O(CR'R")$_r$NR'C(O)R', —(CR'R")$_r$NR"SO$_2$R', —OC(O)NR'R", —NR'C(O)OR", —SO$_2$R', —SO$_2$NR'R", and —NR'SO$_2$R", wherein R' and R" are individually hydrogen, $C_1$-$C_8$ alkyl, cycloalkyl, heterocyclyl, aryl, or arylalkyl, and r is an integer from 1 to 6, or R' and R" together form a cyclic functionality.

Typically, the quaternary ammonium compounds used in the present invention are those having at least two of $R_1$, $R_2$, $R_3$ and $R_4$ being methyl groups and two of $R_1$, $R_2$, $R_3$ and $R_4$ have 8 to about 18 carbon atoms. Exemplary quaternary ammonium compounds include dialkyldimethyl ammonium compounds, and alkyldimethylbenzyl ammonium compounds, where the alkyl groups 8 to 18 carbon atoms. Specific quaternary ammonium compounds include di $C_{8-10}$ alkyldimethylammonium salt and a benzyl $C_{12-16}$ alkyldimethyl ammonium salt. In one embodiment of the invention a mixture of include di $C_{8-10}$ alkyldimethylammonium salt and a benzyl $C_{12-16}$ alkyldimethyl ammonium salt. In a particular embodiment, the di $C_{8-10}$ alkyldimethylammonium salt is a di $C_{8-10}$ alkyldimethylammonium chloride and the benzyl $C_{12-16}$ alkyldimethyl ammonium salt is a benzyl $C_{12-16}$ alkyldimethyl ammonium chloride.

Quaternary ammonium compounds which are useable in the present invention are available from Lonza, Inc., having offices in Allendale, N.J. One particular quaternary ammonium compound combination is Lonzaguard™ Concentrate 75, or other similar quat containing compositions.

Component (iii) is a basic compound with is added to components (i) and (ii) to raise the pH of the composition to above 8. Generally, the pH will be raised to a level which is above about 10.5. Any suitable basic compound may be used; however, it has been discovered that alkanolamines are effective in raising the pH of the composition with adversely affecting the function of the quaternary ammonium compounds. Essentially any alkanolamine may be used, including mono, di and tri alkanolamines. One particularly useful alkanolamine is monoethanolamine. With the addition of the basic component, the disinfectant composition will generally have a pH of the composition is in the range of about 10.5 to about 13.

It has been discovered that when the weight ratio of component (i) to component (ii) is in the range of about 1:1.5 to about 1:10; the weight ratio of component (i) to component (iii) is in the range of about 1:3 to about 1:15, the composition exhibits an under 3 minute disinfecting contacting times. In one embodiment, component (i) to component (ii) is in the range of 1:3 to 1:5 and the weight ratio of component (i) to component (iii) is in the range of 1:5 to 1:8.

The disinfecting composition of the present invention can be supplied as a concentrate, which is diluted to use levels prior to use. The concentrate will have the ratio of components in the amounts expressed above. Alternatively, the disinfecting composition can be provided as a Ready-to-Use (RTU) composition. Whether a RTU composition or a concentrate which is diluted prior to use, the use amount of each of the components in the disinfecting composition should be within the following constraints.

In its use configuration, component (i) is generally present in the composition in an amount from about 400 ppm to about 1200 ppm; component (ii) is present in the composition in an amount from about 2000 to about 3600 ppm; and component (iii) is present in the composition in an amount from about 3000 ppm to about 7000 ppm. In a particular embodiment, component (i) is present in the final use disinfecting composition in an amount from about 600 ppm to about 1000 ppm. Component (ii) is present in the final use disinfecting composition in a more particular embodiment in an amount from about 2600 to about 3200 ppm. Component (iii) is present in the final use disinfecting composition in an amount from about 4000 ppm to about 6000 ppm.

The disinfecting composition may further optionally contain additional ingredients, including surfactants, chelators, builder salts, dyes, fragrances and the like component that are commonly used in the art in cleaning and disinfecting solutions. Suitable surfactants include, but are not limited to, non-ionic surfactants, for example, amine oxides, linear alcohol ethoxylate, secondary alcohol ethoxylates, ethoxylate esters, betamines, polyoxyalkylene polymers and copolymers and alkyl polyglycerides. The surfactants may be present in the disinfecting composition ranges from 0.001 wt. to 10 wt. %, and more typically in the range being 0.01 wt. % to 5 wt. %. Examples of chelators that may be used are sodium and potassium salts of ethylenediaminetetraacetic acid (EDTA), citric acid, nitrilotacetic acid, and various phosphoric acids and zeolites. Chelators serve to remove hardness from the water used as the solvent. The percentage, by weight, of chelators that may be used in the disinfecting composition ranges from 0.001 wt. % to 10 wt. %, and more typically in the range being 0.001 wt. % to 5 wt. %. Examples of building salts that may be used include sodium metasilicate, sodium tripolyphosphate, sodium nitrilotriacetate, sodium carbonate, sodium silicate, citric acid salts and zeolites. The percentage, by weight, of building salts that may be used in the disinfecting composition ranges from 0.001 wt. to 15 wt. %, with the preferred range being 0.001 wt. % to 0.5 wt. %. Other ingredients added to the composition in amounts conventionally used in disinfecting compositions. These components may be present in the concentrate or may be added to the composition during use composition formation.

The disinfecting composition of the present invention may be applied to a substrate to be treated using conventional application techniques. Conventional techniques include spraying, pouring, squirting and/or wiping the disinfecting composition on a substrate. The composition is provided to the end user as a ready-to-use disinfecting composition in is provided to the end user in a container with an application means. For example, the composition may be provided in a container which is pressurized as an aerosol, a container with a trigger or pump sprayer, as a squirt container or conventional containers with a removable cap that allows the user to pour the disinfecting composition onto a substrate.

However, one particularly useful application means is to impregnate the disinfecting composition into a wipe substrate. In this embodiment, the wipe is a single use wipe that is impregnated with the disinfecting composition and is stored in a container that will dispense the wipe to a user. This configuration is generally called a disposable wipe. The container with the wipes may contain a single wipe, or several wipes. Suitable containers include a pouch containing a single wipe, such as a moist towelette which is torn open by the user, or may be a pouch with a resealable opening containing several wipes in a stacked fashion, a rolled fashion or other suitable formation that would allow a single wipe to be removed from the opening at a time. Pouches are generally prepared form a fluid impervious material, such as a film, a coated paper or foil or other similar fluid impervious materials. In another way to dispense wipes of the present invention is to place the wipe in to a fluid impervious container having an opening to access the wipes in the container. Containers may be molded plastic container with lids that are fluid impervious. Generally, the lid will have an opening to access the wipes in the container. The wipe in the container may in a interleaved stacked, such that as a wipe is removed from the container the next wipe is positioned in the opening of the container ready for the user to remove the next wipe. Alternatively, the wipe may be a continuous material which is perforated between the individual wipes of the continuous material. The continuous wipe material with perforations may be in a folded form or may be in a rolled form. Generally, in the rolled form, the wipe material is feed from the center of the rolled material. As with the interleaved stack, as a wipe is removed from the container, the next wipe is positioned in the opening for the use to remove the next wipe, when needed.

Disposable wipes provide advantages over other application vehicles, such as a reusable sponge, rag or the like. Unlike sponges, rags and the like, which are used repeatedly, the impregnated wipe is used a single time and disposed of. As is mentioned above, reused sponge or rag presents problems since the sponge or rags may carry microbes that are not easily killed by the disinfecting composition. Further, disinfecting composition is formulated to treat hard surface, not porous soft surfaces that are present in sponges or rags.

The disinfecting composition is impregnated into the wipe such that the wipe is pre-moistened and will express or release the disinfecting composition on to the substrate as the wipe is run across the substrate to be treated. Generally, the disinfecting composition is saturated into the wipe such that the wipe will release the disinfecting composition to the substrate through the wiping action. Depending on the wipe substrate, saturation was generally achieved using at least about 3 wt. parts of the ready to use disinfecting composition per 1 wt. part of the wipe substrate to be saturated. Generally, the disinfecting composition is used from about 4 parts to 6 parts by weight per 1 part by of the wiper substrate. In these ranges, complete saturation of the substrates can be achieved. It is noted that the amount of the disinfecting solution may go up or down to achieve complete saturation of the wipe substrate, depending on the particular wipe substrate.

Suitable wipe substrates include woven and nonwoven materials. Essentially any nonwoven web material may be used. Exemplary nonwoven materials may include, but are not limited to meltblown, coform, spunbond, airlaid, hydroentangled nonwovens, spunlace, bonded carded webs, and laminates thereof. Optionally, the nonwoven may be laminated with a film material as well. The fibers used to prepare the wipe substrate may be cellulosic fiber, thermoplastic fibers and mixtures thereof. The fibers may also be continuous fibers, discontinuous fibers, staple fibers and mixtures thereof. Basis weights of the nonwoven web may vary from about 12 grams per square meter to 200 grams per square meter or more.

The pre-moistened towelette (wipe) is disclosed herein. In one embodiment the wipe is impregnated with a liquid component containing both active and inert ingredients are within the allowable tolerance levels and the disinfecting composition expressed from the wipe contains active ingredients within the allowable tolerance levels. Once applied to the surface, the antimicrobial disinfecting composition is allowed to remain on the surface for a period of time. The antimicrobial composition may be applied to the surface and allowed to dry or may alternatively be dried by wiping the surface with a dry wipe or wiping device, which is preferably unused.

When the wipe or disinfecting composition of the present invention is used to wipe a surface, disinfection is achieved in less than 4 minutes, generally 3 minutes or less and specifically in 90 seconds or less. It will be understood by those of ordinary skill that the antimicrobial disinfecting composition remains in contact with the surface requiring disinfection for a time sufficient to cause disinfection to occur. It has been discovered that the composition of the present invention is effective against many different microbes, including, but not limited to.

The present invention is further described in detail by means of the following Examples. All parts and percentages are by weight and all temperatures are degrees Celsius unless explicitly stated otherwise.

EXAMPLES

Test Procedure

To test the effectiveness of the compositions of each of the following examples the following test procedure was followed. All tests were conducted using test method for Pre-Saturated Towelette for Hard-Surface Disinfection (Modified AOAC 961.02, AOAC Germicidal Spray Products as Disinfectants).

In each of the following examples, a concentrate mixture of quaternary ammonium compounds is used as the quaternary ammonium containing component in the ready to use composition. The concentrate contains 13% by weight di-$C_{8-10}$ alkyldimethyl ammonium chloride, 8.5% by weight of benzyl $C_{12-16}$ alkyl dimethyl ammonium chloride, 3% by weight tetrasodium ethylenediaminetetraacetate, 72.5% by weight water and 3% by weight ethanol.

Example 1

TABLE 1

| Disinfectant solution. Ingredients | % by Weight |
| --- | --- |
| Deionized water | 97.3 |
| Concentrate described above | 1.6 |
| Polyhexamethylene Biguanidine (PHMB), Vantocil ™ P, 20% | 0.5 |
| Monoethanolamine | 0.60 |
| Total | 100.000 |

The composition of Table 1 had a pH of about 11.6 and was saturated onto a polypropylene nonwoven web having a 34 g/m²±2 g/m² having an EHRT bond pattern, by placing the roll of the polypropylene nonwoven web into a HDPE canister with a snap cap closure and adding such that the container contained about 1 part by weight of the nonwoven web and 5 parts by weight of the composition shown in Table 1.

A wipe was removed from the container and was used to wipe 10 glass slides having the dried bacteria *Staphylococcus aureus* or *Pseudomonas aeruginos*. Each glass slide was contacted with the wipe and the disinfecting solution for 60 seconds. None of the 60 slide containing *Staphylococcus aureus* failed to meet the 5 $Log_{10}$ reduction and the average $Log_{10}$ reduction was 6.48.

Example 2

TABLE 2

| Disinfectant solution. Ingredients | % by Weight |
| --- | --- |
| Deionized water | 97.5 |
| Concentrate described above | 1.6 |
| Polyhexamethylene Biguanidine (PHMB), Vantocil ™ P, 20% | 0.50 |
| Monoethanolamine | 0.40 |
| Total | 100.000 |

The composition of Table 2 had a pH of about 11.6 and was saturated onto a polypropylene nonwoven web having a 34 g/m²±2 g/m² having a EHRT bond pattern, by placing the roll of the polypropylene nonwoven web into a HDPE canister with a snap cap closure and adding such that the container contained about 1 part by weight of the nonwoven web and 4 parts by weight of the composition shown in Table 2.

A wipe was removed from the container and was used to wipe 10 glass slides having the dried bacteria *Staphylococcus aureus* or *Pseudomonas aeruginos*. Each glass slide was contacted with the wipe and the disinfecting solution for 90 seconds. All of the 60 slide containing *Staphylococcus aureus* met the 5 $Log_{10}$ reduction and the average $Log_{10}$ reduction was 6.82. None of the 60 slide containing *Pseudomonas aeruginos* failed to meet the 5 $Log_{10}$ reduction and the average $Log_{10}$ reduction was 6.86.

Comparative Example 1

TABLE 3

| Disinfectant solution. Ingredients | % by Weight |
|---|---|
| Deionized water | 98.43 |
| Concentrate described above | 1.57 |
| Polyhexamethylene Biguanidine (PHMB), Vantocil ™ P, 20% | 0 |
| Monoethanolamine | 0 |
| Total | 100.000 |

The wipe saturated with the composition shown in Table 3 was tested against *Staphylococcus aureus* and 2 of 30 glass slides tested positive for the presence of *S. aureus* after a 3 minute contact time.

Example 3

The compositions described in Examples 1 and 2 were tested against additional bacterial microbes, viruses and a yeast microbes shown in Table 4 using the same test parameters stated above. The results against this organisms are provided in Table 4.

TABLE 4

| Organism | Type | Result |
|---|---|---|
| *Acinetobacter baumannii* | Bacteria | Passed |
| *Acinetobacter baumannii*, MDR | Bacteria | Passed |
| *Burkholderia cepacia* | Bacteria | Passed |
| *Campylobacter jejuni* | Bacteria | Passed |
| *Enterobacter aerogenes* | Bacteria | Passed |
| *Enterococcus faecalis* | Bacteria | Passed |
| *Enterococcus faecalis* (VRE) | Bacteria | Passed |
| ESBL Resistant *Escherichia coli* | Bacteria | Passed |
| ESBL Resistant *Klebsiella pneumoniae* | Bacteria | Passed |
| *Escherichia coli* | Bacteria | Passed |
| *Escherichia coli* - NDM-1 Positive | Bacteria | Passed |
| *Escherichia coli* 0157H: H7 | Bacteria | Passed |
| *Klebsiella pneumoniae* | Bacteria | Passed |
| *Klebsiella pneumoniae* - NDM-1 postive | Bacteria | Passed |
| *Listeria monocytogenes* | Bacteria | Passed |
| *Proteus vulgaris* | Bacteria | Passed |
| *Pseudomonas aeruginosa* | Bacteria | Passed |
| *Salmonella enterica* | Bacteria | Passed |
| *Salmonella typhi* | Bacteria | Passed |
| *Serratia marcescens* | Bacteria | Passed at 10 Minutes |
| *Shigella dysenteriae* | Bacteria | Passed |
| *Staphylococcus aureus* | Bacteria | Passed |
| *Staphylococcus aureus* (CA-MRSA) [300] | Bacteria | Passed |
| *Staphylococcus aureus* (CA-MRSA) [400] | Bacteria | Passed |
| *Staphylococcus aureus* (MDR) | Bacteria | Passed |
| *Staphylococcus aureus* (MRSA) | Bacteria | Passed |
| *Staphylococcus aureus* (VISA) | Bacteria | Passed |
| *Staphylococcus aureus* (VRSA) | Bacteria | Passed |
| *Streptococcus pneumoniae* - Penicillin Resistant | Bacteria | Passed |
| *Streptococcus pyogenes* | Bacteria | Passed |
| *Vibrio cholerae* | Bacteria | Passed |
| Avian Influenza A (H3N2) | Virus | Passed |
| Avian Influenza A (H3N2) | Virus | Passed |
| Hepatitis B Virus | Virus | Passed |
| Hepatitis C Virus | Virus | Passed |
| Herpes Simplex Virus Type 1 | Virus | Passed |
| Herpes Simplex Virus Type 2 | Virus | Passed |
| HIV-1 | Virus | Passed |
| Human Coronavirus (SARS Surrogate) | Virus | Passed |
| Influenza A (H3N2 Hong Kong) | Virus | Passed |
| Influenza A (H7N9) | Virus | Passed |
| Respiratory Syncytial Virus (RSV) | Virus | Passed |
| Rotavirus | Virus | Passed |
| SARS Associated Coronavirus [SARS] [CoV] | Virus | Passed |
| *Candida albicans* | Yeast | Passed |

As can be seen in the forgoing Examples, the compositions of the present invention, with the addition of the biguanide and the basic compound exhibit unexpectedly improved results over a composition not containing these components, even with a longer contact time.

While the invention has been described above with references to specific embodiments thereof, it is apparent that many changes, modifications and variations can be made without departing from the invention concept disclosed herein. Accordingly, it is intended to embrace all such changes, modifications, and variations that fall within the spirit and broad scope of the appended claims.

What is claimed is:

1. A disinfectant composition comprising:
   (i) an antimicrobial biguanide, monoguanide or a combination thereof;
   (ii) a quaternary ammonium compound or a mixture of quaternary ammonium compounds; and
   (iii) a basic compound comprising an alkanolamine;
   wherein the weight ratio of component (i) to component (ii) is in the range of about 1:1.5 to about 1:10; and
   the weight ratio of component (i) to component (iii) is in the range of about 1:3 to about 1:15.

2. The disinfectant composition according to claim 1, wherein the alkanolamine comprises ethanonlamine.

3. The disinfectant composition according to claim 1, wherein the antimicrobial biguanide comprise polyhexamethylene biguanide or salts thereof.

4. The disinfectant composition according to claim 1, wherein the quaternary ammonium compound comprises a dialkyldimethylammonium salt, a benzylalkyldimethylammonium salt or a mixture thereof.

5. The disinfectant composition according to claim 4, wherein the dialkyldimethylammonium salt comprises a di C8-10 alkyldimethylammonium salt and the benzylalkyldimethylammonium salt comprises a benzyl C12-16 alkyldimethyl ammonium salt.

6. The disinfectant composition according to claim 5, wherein the di C8-10 alkyldimethylammonium salt is a di C8-10 alkyldimethylammonium chloride and the benzyl C12-16 alkyldimethyl ammonium salt is a benzyl C12-16 alkyldimethyl ammonium chloride.

7. The disinfectant composition according to claim 1, wherein the antimicrobial biguanide comprise polyhexamethylene biguanide or salts thereof, the quaternary ammonium compound is a mixture of quaternary ammonium compounds comprising a diC8-10 alkyldimethylammonium chloride and a benzyl C12-16 alkyldimethyl ammonium chloride and the basic compound comprises a monoethanolamine.

8. The disinfectant composition according to claim 1, wherein the weight ratio of component (i) to component (ii) is in the range of 1:3 to 1:5 and the weight ratio of component (i) to component (iii) is in the range of 1:5 to 1:8.

9. The disinfectant composition according to claim 7, wherein the weight ratio of component (i) to component (ii) is in the range of 1:3 to 1:5 and the weight ratio of component (i) to component (iii) is in the range of 1:5 to 1:8.

10. The disinfectant composition according to claim 1, wherein the pH of the composition is above 8.

11. The disinfectant composition according to claim 1, wherein the pH of the composition is in the range of about 10.5 to about 13.

12. A disinfectant composition comprising:
(i) an antimicrobial biguanide, monoguanide or a combination thereof;
(ii) a quaternary ammonium compound or a mixture of quaternary ammonium compounds;
(iii) a basic compound comprising an alkanolamine; and
(iv) water;
wherein
component (i) is present in the composition in an amount from about 400 ppm to about 1200 ppm;
component (ii) is present in the composition in an amount from about 2000 to about 3600 ppm; and
component (iii) is present in the composition in an amount from about 3000 ppm to about 7000 ppm.

13. The composition according to claim 12, wherein component (i) is present in the composition in an amount from about 600 ppm to about 1000 ppm;
component (ii) is present in the composition in an amount from about 2600 to about 3200 ppm; and
component (iii) is present in the composition in an amount from about 4000 ppm to about 6000 ppm.

14. The disinfectant composition according to claim 12, wherein the basic compound comprises an alkanolamine.

15. The disinfectant composition according to claim 14, wherein the alkanolamine comprises ethanonlamine.

16. The disinfectant composition according to claim 12, wherein the antimicrobial biguanide comprise polyhexamethylene biguanide or salts thereof.

17. The disinfectant composition according to claim 12, wherein the quaternary ammonium compound comprises a dialkyldimethylammonium salt, a benzylalkyldimethylammonium salt or a mixture thereof.

18. The disinfectant composition according to claim 17, wherein the dialkyldimethylammonium salt comprises a di C8-10 alkyldimethylammonium salt and the benzylalkyldimethylammonium salt comprises a benzyl C12-16 alkyldimethyl ammonium salt.

19. The disinfectant composition according to claim 18, wherein the di C8-10 alkyldimethylammonium salt is a di C8-10 alkyldimethylammonium chloride and the benzyl C12-16 alkyldimethyl ammonium salt is a benzyl C12-16 alkyldimethyl ammonium chloride.

20. The disinfectant composition according to claim 12, wherein the antimicrobial biguanide comprise polyhexamethylene biguanide or salts thereof, the quaternary ammonium compound is a mixture of quaternary ammonium compounds comprising
a di-C8-10 alkyldimethylammonium chloride and a benzyl C12-16 alkyldimethyl ammonium chloride and the basic compound comprises a monoethanolamine.

21. A wipe comprising a substrate which is impregnated with the disinfectant composition of claim 1.

22. The wipe according to claim 21, wherein the substrate comprises meltblown, coform, spunbond, airlaid, hydroentangled nonwovens, spunlace, bonded carded webs, and laminates thereof.

23. A method of disinfecting a surface in need of disinfection, said method comprises applying the disinfectant composition of claim 1 onto a surface in need of disinfection, leaving the composition on the surface for a period of time.

24. The method according to claim 23, wherein the period of time is 3 minutes or less.

25. The method according to claim 24, where the period of time is 90 seconds of less.

26. A method of disinfecting a surface in need of disinfection, said method comprises wiping a surface with the wipe of claim 21, releasing a portion of the disinfectant composition onto a surface in need of disinfection, leaving the composition on the surface for a period of time.

* * * * *